United States Patent
Au et al.

(10) Patent No.: US 6,696,594 B2
(45) Date of Patent: Feb. 24, 2004

(54) PROCESS FOR THE CONVERSION OF ALDEHYDES TO ESTERS

(75) Inventors: Andrew T. Au, Sugar Land, TX (US); Jean-Pierre Lawanier, Houston, TX (US); David Adam Flosser, Stafford, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 1 day.

(21) Appl. No.: 10/144,350

(22) Filed: May 13, 2002

(65) Prior Publication Data

US 2003/0216587 A1 Nov. 20, 2003

(51) Int. Cl.[7] .......................... C07C 67/00; C07C 69/52; C07C 409/00
(52) U.S. Cl. ........................ 560/210; 560/221; 560/238; 560/300
(58) Field of Search ............................... 560/210, 221, 560/238, 300

(56) References Cited

U.S. PATENT DOCUMENTS

| | | | | |
|---|---|---|---|---|
| 3,075,000 A | * | 1/1963 | Castro and Kochi | ....... 260/486 |
| 3,488,394 A | | 1/1970 | Cummins | |
| 3,846,478 A | | 11/1974 | Cummins | |
| 4,007,211 A | | 2/1977 | Trost et al. | |
| 4,110,533 A | | 8/1978 | Woodward et al. | |
| 6,127,556 A | | 10/2000 | Liu et al. | |

OTHER PUBLICATIONS

Zorin et al, "Homolytic Transformations of Alkyl Hypochlorites into Esters" Russian Journal of Chemistry, vol. 33(4), pp. 453–456 (1997).*

Milovanovic et al, "Oxidation of Primary Alcohols to Methyl Esters Using tert–Butyl Hypochlorite, Pyridine and Methyl Alcohol" J. Chem. Soc. Perkin Trans. 2 pages 1231–1233 (1991).*

"A Novel, Nonoxidative Method for the Conversion of Aldehydes to Esters." S.R. Wilson, J. Org. Chem., vol. 47, p. 1360–1361 (1982).

* cited by examiner

Primary Examiner—Mukund J. Shah
Assistant Examiner—Zachary C. Tucker
(74) Attorney, Agent, or Firm—Jim Wheelington

(57) ABSTRACT

A process for the conversion of aldehydes to esters, specifically acrolein or methacrolein to methyl acrylate or methyl methacrylate, respectively. Essentially in the absence of water, an aldehyde is contacted with an oxidizing agent to form an intermediate and then the intermediate is contacted with a diol or an alcohol to form an ester or diester. Preferably, the oxidizing agent is also a chlorinating agent. Specifically, acrolein or methacrolein is contacted with an oxidizing/chlorinating agent, such as t-butyl hypochlorite, and the chlorinated compound is contacted with an alcohol, such as methanol, to form methyl acrylate or methyl methacrylate, respectively. Generally, the order of addition is for the oxidizing agent to be added to the aldehyde, specifically for t-butyl hypochlorite to be added to acrolein or methacrolein, and for the diol or alcohol to be added to the intermediate, specifically for the methanol to be added to the reaction product of acrolein or methacrolein and t-butyl hypochlorite. The process of the present invention can be carried out in the absence or in the presence of solvent. Generally, better methyl acrylate or methyl methacrylate yields are obtained at lower reaction temperatures.

60 Claims, No Drawings

PROCESS FOR THE CONVERSION OF ALDEHYDES TO ESTERS

BACKGROUND OF THE INVENTION

1. Field of the Invention

This invention relates to a process for the conversion of aldehydes to esters, specifically acrolein or methacrolein to methyl acrylate or methyl methacrylate, respectively. In the process, an aldehyde is contacted with an oxidizing agent to form an intermediate and then the intermediate is contacted with a diol or an alcohol to form an ester. Specifically, acrolein or methacrolein is contacted with an oxidizing agent which is also a chlorinating agent, such as t-butyl hypochlorite, and the chlorinated compound is contacted with an alcohol, such as methanol, to form methyl acrylate or methyl methacrylate, respectively.

2. Description of the Prior Art

Manufacture of methyl acrylate (MA) and methyl methacrylate (MMA) can be accomplished by progressive oxidation of propylene to acrolein and to acrylic acid and esterification to methyl acrylate and of isobutylene to methacrolein and methacrylic acid and to methyl methacrylate, respectively. The first oxidation is a catalytic reaction that converts an olefin in the presence of oxygen to an unsaturated aldehyde and water:

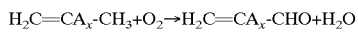

where A is hydrogen or an alkyl group.
The catalyst is generally a multi-component mixed metal oxide catalyst, typically molybdenum based.

The second oxidation is also a catalytic reaction that converts an unsaturated aldehyde in the presence of oxygen to an unsaturated carboxylic acid:

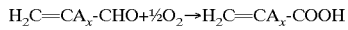

The catalyst is generally a multi-component mixed metal oxide or heteropoly compound catalyst, also typically molybdenum based.

Esterification of the unsaturated carboxylic acid is also a catalytic reaction that converts the unsaturated carboxylic acid in the presence of an alcohol to an unsaturated ester:

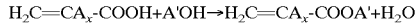

where A' is an alkyl group.

An article entitled "A Novel, Nonoxidative Method for the Conversion of Aldehydes to Esters" by Stephen R. Wilson et al published in J. Org. Chem., vol. 47, pages 1360–1 (1982), disclosed conversion of (cyclobutadiene) iron tricarbonyl to tricarbonyl (methyl 1-4-v-1,3-cyclobutadiene-carboxylate)iron or tricarbonyl (isophorol 1-4-v-1,3-cyclobutadiene-carboxylate)iron with tert-butyl hypochlorite and methanol or isophorol, respectively, and conversion of cinnamaldehyde to methylcinnamate with tert-butyl hypochlorite and methanol. The choice of solvent appeared to control the product obtained. For example, it was reported that the reaction of tert-butyl hypochlorite with cinnamaldehyde in methanol produced 2-chloro-3-methoxy-3-phenylpropanal whereas the reaction of tert-butyl hypochlorite with cinnamaldehyde in carbon tetrachloride produced 1-chloro-3-phenylpropanal. There was no disclosure of the effectiveness of chlorinating aliphatic aldehydes for conversion to esters or of the effect of solvents on such a process.

Hypochlorites have been used in other chemical reactions. U.S. Pat. No. 3,488,394 discloses the hydroxylation of olefins by reacting olefin and a hypochlorite in the presence of $OsO_4$ while U.S. Pat. No. 3,846,478 discloses the reaction of a hypochlorite and olefin in an aqueous medium and in the presence of $OsO_4$ catalyst to hydroxylate the olefin. Both of these procedures can employ co-solvents such as t-butyl alcohol. When this is done, it is disclosed that there is some tendency for allylic chlorination of the olefinic compound to occur, e.g., by the action of t-butyl hypochlorite formed from reaction of the t-butyl alcohol and sodium hypochlorite (NaOCl). Alternatively, part of the t-butyl hypochlorite can react with allyl alcohol to form a chlorinated ether.

U.S. Pat. No. 6,127,556 discloses t-butyl hypochlorite as an oxidizing agent in a multi-step conversion of aldehydes to epoxides.

U.S. Pat. No. 4,110,533 discloses t-butyl hypochlorite in a process for the manufacture of enol derivatives and the conversion of a thio grouping into a sulfoxide grouping by oxidation of a 2-cephem compound to the corresponding oxide in the presence of an inert solvent, such as a halogenated hydrocarbon like methylene chloride.

U.S. Pat. No. 4,007,211 discloses t-butyl hypochlorite in process to convert an alpha-thio carboxylic acid to the corresponding ketone by removing the carboxylic carbon by oxidative decarboxylation.

The conversion of aldehyde to ester without the presence of a metal catalyst would be advantageous. Oxidation of the metal sites can result in poor catalyst performance.

OBJECTS OF THE INVENTION

Accordingly, an object of this invention is to provide a process for converting aldehydes to esters with an oxidizing agent and a diol or an alcohol.

And, an object of this invention is to provide an oxidizing agent, preferably one which is also a chlorinating agent, to form an intermediate of an acyl chloride from an aldehyde.

Also, an object of this invention is to provide an anhydrous process for converting aldehydes to esters.

Further, an object of this invention is to provide a process in the absence of solvents for converting aldehydes to esters.

Additionally, an object of this invention is to provide a process for converting aldehydes to esters in a single batch reactor.

SUMMARY OF THE INVENTION

These and other objects are accomplished by a process for producing esters from aldehydes with an oxidizing agent, preferably one which is also a chlorinating agent, and a diol or an alcohol.

This invention relates to a process for producing esters from aldehydes comprising reacting essentially in the absence of water an aldehyde having the general formula of RCHO, wherein R is an alkenyl group or alkyl group having one to six carbon atoms, with an oxidizing agent having the general formula $R'_3COX$, wherein R' is an alkyl group having one to six carbon atoms bonded to a tertiary carbon atom, each R' being the same or different, and wherein X is a halogen, to form an intermediate and reacting the intermediate with an alcohol having the general formula of R"OH or a diol having the general formula HOR'"OH, wherein R" is an alkyl group or alkoxy group having one to eight carbon atoms or an aryl group having six to ten carbon atoms and R'" is an alkyl group having one to eight carbon atoms or an aryl group having six to ten carbon atoms to form an ester having the general formula RCOOR" or RCOOR'"OH or a diester having the general formula RCOOR'"OOCR.

This invention also relates to a process for producing an ester from an aldehyde comprising (a) contacting an aldehyde having the general formula of RCHO, wherein R is an ethenyl or isopropenyl group, with an oxidizing agent having the general formula R'$_3$COX, wherein R' is an alkyl group having one to six carbon atoms bonded to a tertiary carbon atom, each R' being the same or different, and wherein X is a halogen, to form an intermediate; and (b) contacting an alcohol having the general formula of R"OH or a diol having the general formula HOR'"OH, wherein R" is an alkyl group or alkoxy group having one to eight carbon atoms or an aryl group having six to ten carbon atoms and R'" is an alkyl group having one to eight carbon atoms or an aryl group having six to ten carbon atoms, with the intermediate to form an ester having the general formula RCOOR" or RCOOR'"OH or a diester having the general formula RCOOR'"OOCR wherein the process is carried out essentially in the absence of water.

The reaction sequence of the present invention is as follows:

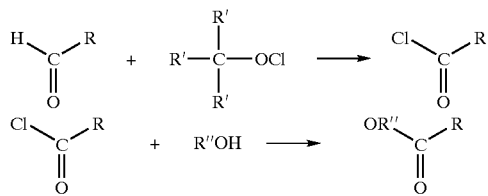

DESCRIPTION OF EMBODIMENTS OF THE INVENTION

This invention is generally a process for converting aldehydes to esters by contacting the aldehyde with an oxidizing agent and then with a diol or an alcohol. The oxidizing agent is preferably also a chlorinating agent such as t-butyl hypochlorite.

To achieve the objects of the present invention, the reaction between the aldehyde and the oxidizing/chlorinating agent should favor free-radical abstraction of hydrogen and replacement with a halogen in the aldehyde group. Subsequently contacting the halogenated intermediate with a diol or an alcohol produces an ester by replacing the halogen with an alkoxy group from the diol or alcohol.

An aldehyde of the general formula of RCHO, R being an alkenyl group or an alkyl group having one to six carbon atoms would be effective in the present invention. Preferably, the aldehyde is acrolein or methacrolein.

An oxidizing agent of the general formula R'$_3$COX wherein R' is an alkyl group having one to six carbon atom bonded to a tertiary carbon atom and X is a halogen would be effective in the present invention. Preferably, R' is a methyl, an ethyl or a propyl group.

Each R' may be the same or different, but preferably all R' are the same. X may be fluorine, chlorine, bromine or iodine but preferably is chlorine. Most preferably, the oxidizing agent is also a chlorinating agent, such as t-butyl hypochlorite.

An alcohol of the general formula of R"OH wherein R" is an alkyl group or an alkoxy group having one to eight carbon atoms or is an aryl group having six to ten carbon atoms would be effective in the present invention. Preferably, the alcohol is methanol, n-butanol, t-butanol, allyl alcohol, 2-ethylhexanol, cyclohexanol, phenol, glycidol, 2-ethoxyethanol or 2-hydroxy ethanol. Most preferably, the alcohol is methanol. A diol of the general formula of HOR'"OH wherein R'" is an alkyl group having one to eight carbon atoms or is an aryl group having six to ten carbon atoms would be effective in the present invention. Preferably, the diol is 1,4-butanediol or ethylene glycol.

An ester of the general formula RCOOR" or RCOOR'"OH or a diester of the general formula RCOOR'"OOCR wherein R, R" and R'" are as defined above could be produced by the process of the present invention. Preferably, if aldehyde is acrolein, the ester is methyl acrylate, t-butyl acrylate, 2-ethylhexyl acrylate, glycidyl acrylate, phenyl acrylate, 2-ethoxyethyl acrylate, 1,4-butanediol monoacrylate, 1,4-butanediol diacrylate, 2-hydroxy monoacrylate or ethylene glycol diacrylate and, if the aldehyde is methacrolein, the ester is methyl methacrylate, n-butyl methacrylate, t-butyl methacrylate, allyl methacrylate, 2-ethylhexyl methacrylate, cyclohexyl methacrylate, phenyl methacrylate or glycidyl methacrylate. Most preferably, the ester is methyl acrylate or methyl methacrylate.

Generally, the aldehyde is contacted with the oxidizing agent while stirring. If the aldehyde is acrolein or methacrolein and the oxidizing agent is t-butyl hypochlorite, the reaction is exothermic. The temperature of the reaction mixture should be maintained in the range from −15 to 75° C., preferably from −5 to 25° C. and most preferably about 25° C. The reaction temperature between acrolein or methacrolein and t-butyl hypochlorite typically would be 15° C.(±)10°C. The molar ratio of t-butyl hypochlorite to acrolein or methacrolein is in the range of 1:0.8 to 1:3, but preferably there is a stoichiometric excess of acrolein or methacrolein. The preferred molar ratio of t-butyl hypochlorite to acrolein or methacrolein is in the range of 1:1.3 to 1:2. Contact time between the acrolein or methacrolein and t-butyl hypochlorite will vary with the amount of reactants but the reaction between acrolein or methacrolein and t-butylhypochlorite should continue until the excess t-butyl hypochlorite or excess acrolein or methacrolein is no longer detectable by gas chromatography or other means of chemical analysis.

Generally, the chlorinated intermediate formed from the aldehyde is contacted with the diol or alcohol, preferably while stirring. If the aldehyde is acrolein or methacrolein and the desired ester is methyl acrylate or methyl methacrylate, the alcohol is methanol. The temperature of the solution when the diol or the alcohol is added is in the range of from 15 to 75° C., more preferably about 25° C. Preferably, the molar ratio of t-butyl hypochlorite:methanol is in the range from 1:2 to 1:25, more preferably in the range from 1:2.25 to 1:17. When the diol or alcohol is contacted with the chlorinated intermediate, hydrogen chloride is formed. Contact time between the chlorinated intermediate and the diol or alcohol will vary with the amount of reactants but the reaction should continue until the presence of the chlorinated intermediate is no longer detectable by gas chromatography or other means of chemical analysis.

Hydrogen chloride is a byproduct of the reaction. The presence of hydrogen chloride may affect the formation of the desired product or cause an unfavorable pH environment. A base may be added before, during or after the addition of the diol or alcohol to neutralize the hydrogen chloride. Preferably, the base is added prior to or concurrently with the addition of the diol or alcohol. The base can be an organic amine, such as pyridine, triethylamine or morpholine, or an inorganic base, such as sodium carbonate or sodium bicarbonate. The base most preferred is sodium bicarbonate. The base is present in the range from 0.5 to 1.5 equivalents relative to t-butyl hypochlorite, preferably in the range from 0.8 to 1.1 equivalents, most preferably about 0.9 equivalents when the diol or alcohol is present in the range from 1.5 to 8.5 equivalents relative to t-butyl hypochlorite, preferably in the range from 2.0 to 5.2 equivalents, most preferably 2.25 equivalents.

The process of the present invention must be carried out in anhydrous conditions, i.e., essentially in the absence of water. The presence of water results in the formation of by-products instead of the desired esters, e.g., acrylic acid or methacrylic acid instead of methyl acrylate or methyl methacrylate.

The process of the present invention can be carried out in the absence or in the presence of solvent. Preferably, solvent is not present. If a solvent is present it should be inert to chlorine. Preferably, the solvent is carbon tetrachloride, chlorobenzene, chloroform, methylene chloride (dichloromethane), tetrachloroethylene or t-butanol and, most preferably, is carbon tetrachloride.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

28.5 mL of carbon tetrachloride and 1.0 g of acrolein (17.8 mmole) were loaded into a three-neck 100 mL nitrogen-purged flask equipped with magnetic stirrer, condenser and thermometer. 2.32 g (21.5 mmole) of t-butyl hypochlorite was then added dropwise over a period of approximately 20 minutes while the temperature was maintained at less than 30° C. by cooling throughout the addition. The reaction mixture was stirred for three hours after which the reaction was considered to be complete because no more t-butyl hypochlorite (t-BuOCl) was detectable by gas chromatography (GC). 2.85 g (89 mmole) of methanol was added over a period of approximately thirty minutes. After approximately 60 minutes the reaction was considered complete. Selectivity of MA was 80.7% by GC.

EXAMPLE 2

The procedure of Example 1 was repeated except 6.611 g of t-butanol was used instead of methanol. The process conditions and yield are shown in Table 1.

EXAMPLE 3

The procedure of Example 1 was repeated except 11.615 g of 2-ethylhexanol was used instead of methanol. The process conditions and yield are shown in Table 1.

EXAMPLE 4

The procedure of Example 1 was repeated except 6.607 g of glycidol was used instead of methanol. The process conditions and yield are shown in Table 1.

EXAMPLE 5

The procedure of Example 1 was repeated except 8.394 g of phenol was used instead of methanol. The process conditions and yield are shown in Table 1.

EXAMPLE 6

The procedure of Example 1 was repeated except 8.038 g of 2-ethoxyethanol was used instead of methanol. The process conditions and yield are shown in Table 1.

EXAMPLE 7

The procedure of Example 1 was repeated except 3.166 g of 1,4-butanediol was used instead of methanol. The process conditions and yield are shown in Table 1.

EXAMPLE 8

The procedure of Example 1 was repeated except 1.608 g of 1,4-butanediol was used instead of methanol. The process conditions and yield are shown in Table 1.

EXAMPLE 9

The procedure of Example 1 was repeated except 5.536 g of 2-hydroxyethanol (ethylene glycol) was used instead of methanol. The process conditions and yield are shown in Table 1.

EXAMPLE 10

The procedure of Example 1 was repeated except 1.036 g of ethylene glycol (2-hydroxyethanol) was used instead of methanol. The process conditions and yield are shown in Table 1. Due to the different amount of ethylene glycol and the different time of the reaction, a different product was obtained than that from Example 9.

TABLE 1

| Example | Acrylate | Temp. (° C.) | Time (hr.) | Yield (%) |
|---|---|---|---|---|
| 2 | t-butyl acrylate | 50–75 | 22 | 42.7 |
| 3 | 2-ethyl hexyl acrylate | 50 | 0.5 | 58 |
| 4 | glycidyl acrylate | 50 | 1.0 | 30.0 |
| 5 | phenyl acrylate | 50 | 1.5 | 59 |
| 6 | 2-ethoxy ethyl acrylate | 50 | 1.0 | 47.9 |
| 7 | 1,4-butanediol monoacrylate | 25 | 1.5 | 53.9 |
| 8 | 1,4-butanediol diacrylate | 25 | 21.15 | 36.1 |
| 9 | 2-hydroxy ethyl monoacrylate | 25 | 44.5 | 40.1 |
| 10 | ethylene glycol diacrylate | 25 | 68 | 58.7* |

*Yield based on ethylene glycol

EXAMPLE 11

300 mL of carbon tetrachloride and 21.05 g of methacrolein (0.30 mole) were loaded into a three-neck 500 mL nitrogen-purged flask equipped with magnetic stirrer, condenser and thermometer.

32.57 g (0.30 mole) of t-butyl hypochlorite was then added dropwise by addition funnel over a period of approximately 30 minutes at room temperature. The temperature was maintained at less than 40° C. by cooling throughout the addition. The reaction mixture was then heated to 50° C. and maintained at that temperature for approximately 5–6 hours until t-butyl hypochlorite (t-BuOCl) was no longer detectable by gas chromatography (GC). The mixture was then cooled to room temperature and 150 mL (3.75 mole) of methanol was added dropwise by addition funnel over a period of approximately thirty minutes. The mixture was cooled with an ice/water mixture during the addition. After approximately 30–60 minutes the reaction was considered complete. Selectivity of MMA was 80–85% by GC.

EXAMPLE 12

The procedure of Example 11 was repeated except 28.5 mL of carbon tetrachloride, 1 g of methacrolein, 1.85 g of t-butyl hypochlorite and 2.64 g of n-butanol (instead of methanol) were used. The process conditions and yield are shown in Table 2.

EXAMPLE 13

The procedure of Example 12 was repeated except a mixture of 5.287 g of t-butanol and 2.021 g of triethylamine was used instead of n-butanol. The process conditions and yield are shown in Table 2.

EXAMPLE 14

The procedure of Example 12 was repeated except 20.716 g of allyl alcohol was used instead of n-butanol. The process conditions and yield are shown in Table 2.

EXAMPLE 15

The procedure of Example 12 was repeated except 9.29 g of 2-ethylhexanol was used instead of n-butanol. The process conditions and yield are shown in Table 2.

EXAMPLE 16

The procedure of Example 12 was repeated except 7.145 g of cyclohexanol was used instead of n-butanol. The process conditions and yield are shown in Table 2.

EXAMPLE 17

The procedure of Example 12 was repeated except 6.714 g of phenol was used instead of n-butanol. The process conditions and yield are shown in Table 2.

EXAMPLE 18

The procedure of Example 12 was repeated except 5.285 g of glycidol was used instead of n-butanol. The process conditions and yield are shown in Table 2.

TABLE 2

| Example | Methacrylate | Diol/Alcohol | Reaction Conditions | Time (hr.) | Yield (%) |
|---|---|---|---|---|---|
| 12 | n-butyl methacrylate | n-butanol | same as Example 11 | 18.5 | 56.3 |
| 13 | t-butyl methacrylate | t-butanol | added TEA | 19.5 | 57.4 |
| 14 | allyl methacrylate | allyl alcohol | same as Example 11 | 15.5 | 88.1 |
| 15 | 2-ethylhexyl methacrylate | 2-ethyl hexanol | same as Example 11 | 1.5 | 69.8 |
| 16 | cyclohexyl methacrylate | cyclohexanol | same as Example 11 | 2 | 47.4 |
| 17 | phenyl methacrylate | phenol | same as Example 11 | 2 | 50.4 |
| 18 | glycidyl methacrylate | glycidol | same as Example 11 | 2.5 | 41.1 |

As the above examples illustrate, the process of the present invention can be used to prepare several esters by using different diols or alcohols and different aldehydes.

EXAMPLE 19

A three-neck, round-bottomed 50 mL flask equipped with a magnetic stirring bar, a nitrogen gas inlet, a pressure-equalizing addition funnel wrapped in aluminum foil and a thermometer was charged with 4.046 g (0.05780 mol) of methacrolein and cooled to 10° C. with dry ice in acetone. To the stirred methacrolein, under a nitrogen blanket, was added 3.971 g (0.03660 mole) of tert-butyl hypochlorite, dropwise over a 30 minute period via the addition funnel. The dry ice/acetone bath was used to keep the exothermic reaction at 10° C. After the addition was complete, the reaction mixture was stirred for an additional 1.5 hour at 10° C., then warmed to 25° C. To the reaction mixture was added 2.732 g (0.03252 mol) of 99.99+% sodium bicarbonate followed by 3.45 mL (2.73 g, 0.0853 mol) of anhydrous methanol. This mixture was stirred at 25° C. for 1.25 hour. Methyl methacrylate yield was 90%, unreacted methacrolein recovery was 89% (with the most of the remainder lost as the acetal of methacrolein which is easily converted back to methacrolein). Methacrylic acid (MAA) was also obtained at 5.6% and can be easily converted to MMA (Yields by gas chromatography using 1,2,3-trichloropropane as an internal standard).

EXAMPLE 20

The procedure of Example 19 was repeated except the addition time for hypochlorite was 2 hours at −5° C., stirring was for 1 hours at 10° C. and 17 equivalents of methanol were added. The process conditions and yield are shown in Table 3.

EXAMPLE 21

The procedure of Example 19 was repeated except the addition time for hypochlorite was 2 hours at −5° C., stirring was for 1 hour at −5° C. and 1 hours at 10° C., 17 equivalents of methanol were added and no sodium bicarbonate was used. The process conditions and yield are shown in Table 3.

EXAMPLE 22

The procedure of Example 19 was repeated except the addition of hypochlorite was 2 hours at −5° C., stirring was 1 hour at 10° C., 17 equivalents of methanol were added and pyridine at 1.1 equivalents was used instead of sodium bicarbonate. The process conditions and yield are shown in Table 3.

EXAMPLE 23

The procedure of Example 19 was repeated except the addition time for t-butyl hypochlorite was 0.33 hour at −5° C. and stirring was 0.5 hour at −5° C. and 1 hour at 10° C.

EXAMPLE 24

The procedure of Example 19 was repeated except the addition time for t-butyl hypochlorite was 0.5 hour at −5° C., stirring was 0.5 hour at −5° C. and 1 hour at 10° C. and 0.8 equivalents of sodium bicarbonate were added. The process conditions and yield are shown in Table 3.

EXAMPLE 25

The procedure of Example 19 was repeated except the addition time for t-butyl hypochlorite was 0.5 hour at −50° C. to 2 equivalents of methacrolein and stirring was 0.5 hour at −5° C. and 1 hour at 10° C.

The process conditions and yield are shown in Table 3.

EXAMPLE 26

The procedure of Example 19 was repeated except the addition time for t-butyl hypochlorite was 0.33 hour to 1.3 equivalents of methacrolein. The process conditions and yield are shown in Table 3.

EXAMPLE 27

The procedure of Example 19 was repeated except the addition temperature and time for t-butyl hypochlorite was 25° C. and 0.83 hour and stirring was 1 hour at 25° C. The process conditions and yield are shown in Table 3.

EXAMPLE 28

The procedure of Example 19 was repeated except the reaction was maintained at room temperature (about 25° C.), the hypochlorite was added over a fifteen minute period and the sodium bicarbonate and methanol were added fifteen minutes after the hypochlorite addition was complete.

EXAMPLE 29

The procedure of Example 27 was repeated except the reaction was maintained at 40° C.

EXAMPLE 30

The procedure of Example 27 was repeated except the reaction was maintained at 5° C.

EXAMPLE 31

A 3-neck, 50 mL round-bottom flask equipped with a magnetic stirring bar, a nitrogen gas inlet, a septum and a thermometer was charged with 4.745 g (0.04373 mol) of tert-butyl hypochlorite and cooled to −5° C. with dry ice in acetone. To the stirred tert-butyl hypochlorite was added, under a nitrogen blanket, 2.770 (0.03957 mol) of methacrolein continuously over a two hour period via a syringe pump. The dry ice/acetone bath was used to keep the exothermic reaction at −5° C. After the addition was complete, the reaction mixture was stirred for an additional two hours at 25° C. To the reaction mixture was then added 20.6 g of anhydrous methanol. This mixture was stirred at 25° C. for 20 minutes. Yield of MMA was 69% by GC using 1,2,3-trichloropropane as an internal standard.

EXAMPLE 32

A 3-neck, 25 mL round-bottomed flack equipped with a magnetic stirring bar, a nitrogen gas inlet and a thermometer was charged with 0.518 g (0.00740 mol) of methacrolein, 0.991 g (0.00913 mol) of tert-butyl hypochlorite and 12 mL of $CCl_4$ under a blanket of nitrogen. The reaction mixture was cooled to 10° C. and stirred at this temperature overnight. After warming to room temperature, the mixture was added dropwise to 5.306 g (0.1658 mol) of methanol and stirred for one hour at room temperature. Yield of MMA was 62% by GC using 1,2,3-trichloropropane as an internal standard.

TABLE 3

| EX. | TBH:M mol ratio | $Time_1/T_1$ hr/° C. | $Time_2/T_2$ hr/° C. | MeOH eqv. | MMA Yield (%) | M Rec. (%) | Base eqv. | MAA (%) |
|---|---|---|---|---|---|---|---|---|
| 20 | 1:1.5 | 2/−5 | 1/10 | 17 | 81 | 74 | 0.9 | 0 |
| 21 | 1:1.5 | 2/−5 | 1/−5 1/10 | 17 | 83 | 17 | None | 0 |
| 22 | 1:1.5 | 2/−5 | 1/10 | 17 | 78 | 47 | 1.1* | — |
| 23 | 1:1.5 | 0.33/−5 | 0.5/−5 1/10 | 2.25 | 90 | 91 | 0.9 | 6 |
| 24 | 1:1.5 | 0.5/−5 | 0.5/−5 1/10 | 2.25 | 89 | 79 | 0.8 | 5.4 |
| 25 | 1:2 | 0.5/−5 | 0.5/−5 1/10 | 2.25 | 88 | 85 | 0.9 | 7 |
| 26 | 1:1.3 | 0.33/10 | 1.5/10 | 2.25 | 88 | 93 | 0.9 | 6 |
| 27 | 1:1.5 | 0.83/25 | 1/25 | 2.25 | 81 | 90 | 0.9 | 6.5 |
| 28 | 1:1.5 | 0.25/25 | 0.25/25 | 2.25 | 89 | 92 | 0.9 | 5.5 |
| 29 | 1:1.5 | 0.25/40 | 0.25/40 | 2.25 | 76 | 89 | 0.9 | 3 |
| 30 | 1:1.5 | 0.25/50 | 0.25/50 | 2.25 | 54 | 43 | 0.9 | 4 |
| 31 | 1.1:1 | 2/−5 | 2/25 | 17 | 69 | N/A | None | 0 |
| 32 | 1.23/1 | N/A | 24/10 | 22 | 62 | N/A | None | 0 |

TBH—tert-butyl hypochlorite
M—methacrolein
$T_1$—temperature of addition of TBH to M
$Time_1$—time of addition of TBH to M
$Time_2$—time of stirring after addition of TBH to M
$T_2$—temperature during stirring after addition of TBH to M
MeOH—methanol
eqv.—equivalents relative to TBH
MMA—methyl methacrylate
*—Pyridine instead of $NaHCO_3$
MAA—methacrylic acid In the Examples above, it should be noted that methacrylic acid is easily convertible to methyl methacrylate, so the total yield to methyl methacrylate is potentially the sum of the MMA Yield and the MAA%.

Examples 19 and 28–30 demonstrate the effect of temperature on MMA yield. Generally, better MMA yields are obtained at lower reaction temperatures. While the claimed process is effective in obtaining acceptable MMA yields at reaction temperatures between −5 and 50° C., better results are realized at a temperature in the range from −5 to 25° C. and, most preferably, at a temperature of about 25° C. Because the reaction is exothermic, it is necessary to cool the reaction vessel to maintain the reaction temperature. Due to reaction kinetics which may vary during the course of the reaction and to the effect of the amount of the reactants relative to each other (stoichiometric v. excess), the temperature may vary during the course of the reaction by ±10° C. A typical temperature is 15° C.(±)10° C.

Examples 31 and 32 demonstrate that the preferred order of addition is for the oxidizing agent to be added to the aldehyde, specifically for t-butyl hypochlorite to be added to methacrolein, and for the diol or alcohol to be added to the intermediate, specifically for the methanol to be added to the reaction product of methacrolein and t-butyl hypochlorite.

Obviously, numerous modifications and variations of the present invention are possible in light of the above teachings. It is therefore to be understood that within the scope of the appended claims, the invention may be practiced otherwise than as specifically described herein.

What is claimed is:

1. A process for producing esters from aldehydes comprising reacting essentially in the absence of water an aldehyde having the general formula of RCHO, R being an alkenyl group or alkyl group having one to six carbon atoms, with an oxidizing agent having the general formula $R'_3COX$, wherein R' is an alkyl group having one to six carbon atom bonded to a tertiary carbon atom, each R' being the same or different, and wherein X is a halogen, to form an intermediate which is reacted with an alcohol having the general formula of R"OH wherein R" is an alkyl group or an alkoxy group having one to eight carbon atoms or is an aryl group having six to ten carbon atoms or with a diol having the general formula HOR'''OH wherein R''' is an alkyl group having one to eight carbon atoms or is an aryl group having six to ten carbon atoms to form an ester having the general formula RCOOR" or RCOOR'''OH or a diester having the general formula RCOOR'''OOCR, wherein a base is optionally added before, during or after the alcohol or diol and the base is an inorganic base.

2. The process of claim 1 wherein R' is a methyl group, an ethyl group or a propyl group.

3. The process of claim 1 wherein all R' are the same.

4. The process of claim 1 wherein X is chlorine.

5. The process of claim 1 wherein R' is a methyl group and all R' are the same.

6. The process of claim 1 wherein the oxidizing agent is t-butyl hypochlorite.

7. The process of claim 1 wherein the aldehyde is acrolein.

8. The process of claim 7 wherein the alcohol is methanol and the ester is methyl acrylate.

9. The process of claim 7 wherein the alcohol is t-butanol and the ester is t-butyl acrylate.

10. The process of claim 7 wherein the alcohol is 2-ethylhexanol and the ester is 2-ethylhexyl acrylate.

11. The process of claim 7 wherein the alcohol is glycidol and the ester is glycidyl acrylate.

12. The process of claim 7 wherein the alcohol is phenol and the ester is phenyl acrylate.

13. The process of claim 7 wherein the alcohol is 2-ethoxyethanol and the ester is 2-ethoxyethyl acrylate.

14. The process of claim 7 wherein the alcohol is 1,4-butanediol and the ester is 1,4-butanediol monoacrylate.

15. The process of claim 7 wherein the alcohol is 1,4-butanediol and the ester is 1,4-butanediol diacrylate.

16. The process of claim 7 wherein the alcohol is 2-hydroxyethanol and the ester is 2-hydroxyethyl monoacrylate.

17. The process of claim 7 wherein the diol is ethylene glycol and the ester is ethylene glycol diacrylate.

18. The process of claim 1 wherein the aldehyde is methacrolein.

19. The process of claim 18 wherein the alcohol is methanol and the ester is methyl methacrylate.

20. The process of claim 18 wherein the alcohol is n-butanol and the ester is n-butyl methacrylate.

21. The process of claim 18 wherein the alcohol is t-butanol and the ester is t-butyl methacrylate.

22. A process for producing esters from aldehydes comprising reacting essentially in the absence of water methacrolein with an oxidizing agent having the general formula $R'_3COX$, wherein R' is an alkyl group having one to six carbon atom bonded to a tertiary carbon atom, each R' being the same or different, and wherein X is a halogen, to form an intermediate which is reacted with allyl alcohol to form allyl methacrylate.

23. The process of claim 18 wherein the alcohol is 2-ethylhexanol and the ester is 2-ethylhexyl methacrylate.

24. The process of claim 18 wherein the alcohol is cyclohexanol and the ester is cyclohexyl methacrylate.

25. The process of claim 18 wherein the alcohol is phenol and the ester is phenyl methacrylate.

26. The process of claim 18 wherein the alcohol is glycidol and the ester is glycidyl methacrylate.

27. A process for producing an ester from an aldehyde comprising:
    (a) contacting an aldehyde having the general formula of RCHO, wherein R is an ethenyl or a isopropenyl group, with an oxidizing agent having the general formula $R'_3COX$, wherein R' is an alkyl group having one to six carbon atom bonded to a tertiary carbon atom and X is a halogen, to form an intermediate; and
    (b) contacting an alcohol having the general formula of R"OH, wherein R" is an alkyl group or an alkoxy group having one to eight carbon atoms or is an aryl group having six to ten carbon atoms or contacting a diol having the general formula HOR'''OH, wherein R''' is an alkyl group having one to eight carbon atoms or is an aryl group having six to ten carbon atoms, with the intermediate to form an ester having the general formula RCOOR' or RCOOR'''OH or a diester having the general formula RCOOR'''OOCR wherein the process is carried out essentially in the absence of water.

28. The process of claim 27 wherein the aldehyde is acrolein, the alcohol is methanol and the ester is methyl acrylate.

29. The process of claim 27 wherein the aldehyde is methacrolein, the alcohol is methanol and the ester is methyl methacrylate.

30. The process of claim 27 wherein R' is a methyl group, an ethyl group or a propyl group.

31. The process of claim 27 wherein all R' are the same.

32. The process of claim 27 wherein X is chlorine.

33. The process of claim 27 wherein R' is a methyl group and all R' are the same.

34. The process of claim 27 wherein the oxidizing agent is t-butyl hypochlorite.

35. The process of claim 27 wherein the process additionally comprises contacting the aldehyde with the t-butyl hypochlorite at a temperature in the range of from −15 to 75° while stirring.

36. The process of claim 35 wherein the temperature is in the range of from −5 to 50°.

37. The process of claim 36 wherein the temperature is in the range of from −5 to 25 ° C.

38. The process of claim 36 wherein the temperature is about 25 ° C.

39. The process of claim 36 wherein the temperature is 15° C.(+/−)10° C.

40. The process of claim 28 wherein the process additionally comprises contacting the acrolein with the t-butyl hypochlorite while stirring until acrolein or t-butyl hypochlorite is no longer detectable by gas chromatography.

41. The process of claim 29 the process additionally comprises contacting the methacrolein with the t-butyl hypochlorite while stirring until methacrolein or t-butyl hypochlorite is no longer detectable by gas chromatography.

42. The process of claim 28 wherein the molar ratio of t-butyl hypochlorite:acrolein is in the range of 1:1 to 1:3.

43. The process of claim 29 wherein the molar ratio of t-butyl hypochlorite:methacrolein is in the range of 1:1 to 1:3.

44. The process of claim 27 wherein the temperature of the solution when the diol or alcohol is added is in the range of from 15 to 75° C.

45. The process of claim 44 wherein the temperature of the solution when diol or alcohol is added is about 25° C.

46. The process of claim 27 wherein the process additionally comprises adding a base before, during or after the addition of diol or alcohol.

47. The process of claim 46 wherein the base is an organic amine or an inorganic base.

48. The process of claim 47 wherein the base is pyridine, triethylamine or morpholine.

49. The process of claim 47 wherein the base is sodium carbonate or sodium bicarbonate.

50. The process of claim 49 wherein the base is sodium bicarbonate.

51. The process of claim 28 wherein the molar ratio of t-butyl hypochlorite:methanol is in the range from 1:1 to 1:22.

52. The process of claim 51 wherein the molar ratio of acrolein:methanol is in the range from 1:1 to 1:17.

53. The process of claim 29 wherein the molar ratio of methacrolein:methanol is in the range from 1:1 to 1:22.

54. The process of claim 53 wherein the molar ratio of methacrolein:methanol is in the range from 1:1 to 1:17.

55. The process of claim 27 wherein the process occurs in the absence of solvent.

56. The process of claim 27 wherein the process additionally comprises an inert solvent.

57. The process of claim 56 wherein the inert solvent is carbon tetrachloride, chlorobenzene, chloroform, dichloromethane, tetrachioroethylene or t-butanol.

58. The process of claim 57 wherein the inert solvent is carbon tetrachloride.

59. The process of claim 27 wherein the oxidizing agent is added to the aldehyde.

60. The process of claim 27 wherein the diol or alcohol is added to the intermediate.

* * * * *